United States Patent
Friedrich

[11] Patent Number: 5,855,607
[45] Date of Patent: Jan. 5, 1999

[54] IMPLANT FOR MEDIALISATION OF VOCAL CORD

[75] Inventor: Gerhard Friedrich, Graz, Austria

[73] Assignee: Heinz Kunz GmbH Medizintechnik, Dusslingen, Germany

[21] Appl. No.: 938,201

[22] Filed: Sep. 26, 1997

[30] Foreign Application Priority Data

Sep. 27, 1996 [DE] Germany .................. 296 16 828 U

[51] Int. Cl.⁶ .................................................. A61F 2/20
[52] U.S. Cl. ............................................................ 623/9
[58] Field of Search ...................................... 623/9

[56] References Cited

U.S. PATENT DOCUMENTS 5,197,982  3/1993  Goldsmith, III et al. ............... 623/9
5,306,298  4/1994  Godley, III et al. ................... 623/9
5,344,453  9/1994  Montgomery .......................... 623/9

FOREIGN PATENT DOCUMENTS 0 535 833 A1  4/1993  European Pat. Off. .

Primary Examiner—Randy C. Shay
Attorney, Agent, or Firm—Michael J. Striker

[57] ABSTRACT

An implant for medialization of vocal cords after vocal cord paralysis, to be inserted into an opening of a shield cartilage formed by operation, the implant has an element which is bent from a metal strip and has a central part adapted to abut against a vocal cord and two hook-shaped end regions adapted to engage around edges of a shield cartilage opening, the metal strip having a bend arranged between the central part and at least one of the hook-shaped end regions and adapted to be located between a protective cartilage and the vocal cord after insertion of the implant.

5 Claims, 1 Drawing Sheet

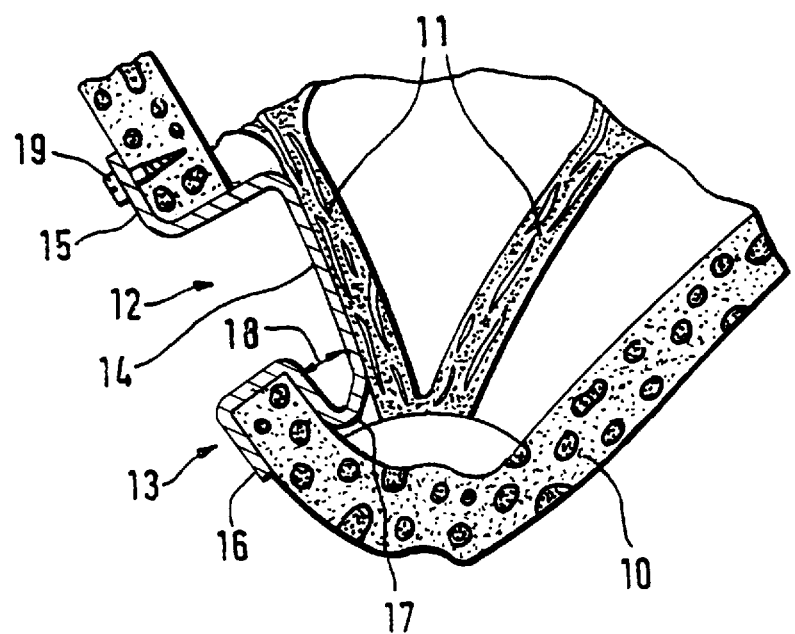

IMPLANT FOR MEDIALISATION OF VOCAL CORD

BACKGROUND OF THE INVENTION

The present invention generally relates to an implant for medialisation of vocal cords.

More particularly, it relates to an implant for medialisation of vocal cords, in particular after a vocal cords paralysis, which is insertable into an opening made in shield cartilage by an operation.

Such implants serve for narrowing the vocal gap in the case of the cord paralysis and for bringing the vocal cords from their lateral position again into the center line. For this purpose an opening is formed in the shield cartilage, and the implant is inserted through the opening so as to medialise the vocal cords.

The disadvantage of known predominantly used implants is certain objections against the utilized material. This implant must be cut out by a surgeon from a silicone block. There use is therefore time-consuming and the forming of the implant is not always optimal. Moreover, the fixing of the implant is difficult so that a displacement is possible. Such a displacement of the implant, for example into the interior of the larynx can have life-threatening consequences since it can interrupt the breathing.

SUMMARY OF THE INVENTION

Accordingly, it is an object of present invention to provide an implant for medialisation of vocal cords, which avoids the disadvantages of the prior art.

More particularly, it is an object of present invention to provide an implant for medialisation of vocal cords which can be introduced with a standardized technique during the operation under local anesthesia of the patient fast and reliable, and the degree of medialisation is individually adjustable.

In keeping with these objects and with others which will become apparent hereinafter, one feature of present invention resides, briefly stated, in an implant for medialisation of vocal cords, which implant has an element bent from a metal strip and having a central part adapted to abut against the vocal cords and hook-shaped end regions engaging the edges of the shield cartilage opening, wherein a bend of the metal strip is arranged between the central part and at least one of the hook-shaped end regions, to be located between the shield cartilage and the vocal cord after insertion of the implant.

By changing the radius of the bend, the pressure of the central part against the vocal cord can be varied. Furthermore, the pressure can be varied in a small region, so that the total implant is changed as to its distance to the vocal cords.

In order to perform this type of adjustment of the pressure of the implant, at least one of the hook-shaped end regions can be mountable on the shield cartilage by an adjusting screw, in accordance with another feature of the present invention.

In accordance with still another feature of present invention, in order to avoid rejection reactions of the body, the implant can be composed either of a body-tolerable metal and/or provided with a body-tolerable coating. A material for the implant can be for example a titanium sheet or also gold or high grade steel sheet.

A special advantage of the inventive implant is that, after its insertion in the shield cartilage it can be positioned reliably so that a displacement of the implant which could reach the airways with life-threatening complications, is no longer possible. This is achieved by the special shaping of the implant and bending of the metal ends, and can be further secured by fixing of the implant with the adjusting screw on the shield cartilage.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

The single FIGURE of the drawings is a view showing an implant for medialisation of vocal cords, in accordance with the present invention.

DESCRIPTION OF PREFERRED EMBODIMENTS

The FIGURE of the drawings is a view showing an implant for medialisation of vocal cords, in accordance with the present invention.

The FIGURE of the drawings shows a partial section of a human larynx. A shield cartilage 10 can be clearly seen in the front region of the larynx. Vocal cords 11 extend from the shield cartilage 10 to adjusting cartilages which are not shown in detail. An opening 12 is formed in the shield cartilage 10 for insertion an implant for one of the vocal cords 11.

The implant is identified as a whole with reference numeral 13. It is bent from a metal strip. The implant has a central part 14 against which the vocal cord 11 abuts. The implant further has end regions 15 and 16 which are hook-shaped and engage over the edges of the opening 12 in the shield cartilage 10.

A bend 17 is formed in the metal strip between the central part 14 and the lower hooked-shaped region 16 of the implant 13. The bend 17 is located between the shield cartilage 10 and the vocal cord 11 and produces a pre-tensioning of the central part 14 against the vocal cord 11. The degree of pre-tensioning can be varied by changing the radius of the bend 17, as identified with a double arrow 18.

A displacement of the central part 14 in direction toward the vocal cord 11 leads to an increase in the pre-tensioning of the central part 14. This displacement can be performed by an adjusting screw 19. The adjusting screw 19 connects the end region 15 of the implant 13 with the shield cartilage 10.

In the shown implant the pre-tensioning of the central part 14 relative to the vocal cord 11 can be performed either by bending or compressing the bend 17, or by adjusting the screw 19 during the operation of the patient under local anesthesia. In correspondence with the results of vocal tests which are constantly performed with the patient, it is therefore possible to provide an optimal pre-tensioning of the implant 13 and thereby an optimal support of the vocal cord 11.

It will be understood that each of the elements described above, or two or more together, may also find a useful application in other types of constructions differing from the types described above.

While the invention has been illustrated and described as embodied in implant for medialisation of vocal cords, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An implant for medialisation of vocal cords after vocal cord paralysis, to be inserted into an opening of a shield cartilage formed by operation, the implant comprising an element which comprises a bent metal strip and has a central part adapted to abut against a vocal cord and two hook-shaped end regions adapted to engage around edges of a shield cartilage opening, said metal strip having a bend arranged between said central part and at least one of said hook-shaped end regions, said bend being adapted to be located between a protective cartilage and the vocal cord after insertion of the implant.

2. An implant as defined in claim 1; and further comprising an adjusting screw for mounting at least one of said hook-shaped end regions on the shield cartilage.

3. An implant as defined in claim 1, wherein said metal strip is composed of a material which is tolerable by a human body.

4. An implant as defined in claim 1, wherein said metal strip is covered with a coating which is tolerable by a human body.

5. An implant as defined in claim 1, wherein said metal strip is composed of a titanium sheet.

* * * * *

UNITED STATES PATENT AND TRADEMARK OFFICE
CERTIFICATE OF CORRECTION

PATENT NO. : 5,855,607
DATED     : January 5, 1999
INVENTOR(S): Gerhard Friedrich It is certified that error appears in the above-identified patent and that said Letters Patent is hereby corrected as shown below:

On the title page, item [73], change "Kunz" to --Kurz--.

Signed and Sealed this

Sixth Day of July, 1999

*Attest:*

Q. TODD DICKINSON

*Attesting Officer*   *Acting Commissioner of Patents and Trademarks*